United States Patent [19]

Eppstein et al.

[11] Patent Number: 4,684,625

[45] Date of Patent: * Aug. 4, 1987

[54] METHOD FOR ENHANCING THE ANTI-INFECTIVE ACTIVITY OF MURAMYLDIPEPTIDE DERIVATIVES

[75] Inventors: Deborah A. Eppstein, Palo Alto; Elizabeth Fraser-Smith, Los Altos; Thomas R. Matthews, Los Gatos, all of Calif.

[73] Assignee: Syntex (U.S.A.) Inc., Palo Alto, Calif.

[*] Notice: The portion of the term of this patent subsequent to Jun. 11, 2002 has been disclaimed.

[21] Appl. No.: 725,037

[22] Filed: Apr. 19, 1985

Related U.S. Application Data

[63] Continuation-in-part of Ser. No. 396,213, Jul. 8, 1982, Pat. No. 4,522,811.

[51] Int. Cl.⁴ .......................... C07K 5/06; A61K 9/42
[52] U.S. Cl. ........................................ 514/19; 424/38; 514/8; 536/4.1; 536/53
[58] Field of Search ................... 514/8, 19; 424/38

[56] References Cited

U.S. PATENT DOCUMENTS 4,522,811 6/1985 Eppstein et al. .................. 514/2

OTHER PUBLICATIONS

Masek et al., *Experientia*, 34(10), 1363–64 (1978).
Kotani et al., *Biken Journal*, 18, 105–111 (1975).
Kotani et al., *Biken Journal*, 20, 95–103 (1977).
Ledrer, *J. of Med. Chem.*, 23, No. 8, 819–824 (1980).
Parent et al., *Infection and Immunity*, 27, No. 2, 826–831 (1980).

*Primary Examiner*—Johnnie R. Brown
*Assistant Examiner*—F. T. Moezie
*Attorney, Agent, or Firm*—Grant D. Green; Tom M. Moran; Alan M. Krubiner

[57] ABSTRACT

Co-administration of a muramyldipeptide derivative with liposomes enhances the anti-infective activity of the muramyldipeptide derivative.

26 Claims, No Drawings

METHOD FOR ENHANCING THE ANTI-INFECTIVE ACTIVITY OF MURAMYLDIPEPTIDE DERIVATIVES

This is a continuation in part of copending U.S. patent application Ser. No. 396,213, filed July 8, 1982, now U.S. Pat. No. 4,522,811.

BACKGROUND OF THE INVENTION

1. Field of the Invention

This invention relates to a method for enhancing the anti-infective activity of muramyldipeptide derivatives using liposomes.

2. Related Disclosures

In the field of immunology, multiple injections of a vaccine or bacterin are frequently required to produce the immunological response in a subject sufficient to ward off an infection. During the development of the vaccine art, researchers discovered that substances could be added to the vaccine composition which would enhance the immunogenicity of the vaccine, resulting in an immune response superior to that achieved by administering the antigen alone. Compounds which enhance the antigenicity of an antigen are known as adjuvants. Among the most effective adjuvants developed early in the vaccine art is Freund's complete adjuvant, which is a suspension of killed, whole *Mycobacterium tuberculosis* emulsified in mineral oil. Also highly effective is Freund's incomplete adjuvant, which is a mineral oil emulsion without mycobacteria. These two adjuvants are used as laboratory standards, but are not used commercially because Freund's complete adjuvant contains the microorganism *M. tuberculosis*, and both the complete and incomplete forms contain mineral oil, which is known to produce granulomas and other toxic effects. Also, in the absence of the mycobacteria, the incomplete adjuvant does not always produce a satisfactorily high immunogenic enhancement.

The basic units responsible for enhancing the cellular antigenicity response are believed to be the sugar-containing peptides of the mycobacterial cell wall. A detailed study of the chemistry of mycobacterial cell wall resulted in the observation by F. Ellouz, et al., *Biochem. Biophys. Res. Comm.*, 59, 1317 (1974) that the adjuvant activity could be directly attributed to the bacterial wall peptidoglycan derivatives. The smallest effective molecule was found to be an N-acetylmuramyldipeptide, specifically N-acetylmuramyl-L-alanyl-D-isoglutamine. See C. Messer, P. Sinay, and A. Adams, *Biochem. Biophys. Res. Comm.*, 66, 1316 (1975). This compound is now commonly called muramyldipeptide or MDP.

Subsequently, a number of muramyldipeptide analogs and derivatives were prepared by various academic and industrial concerns. The majority of these derivatives have been demonstrated to have some degree of immunopotentiating activity. In addition, many of these muramyldipeptide derivatives are per se active in enhancing the host immunity against infectious organisms such as *Klebsiella pneumonia, Escherichia coli, Candida albicans, Staphylococcus aureus* and the like. The literature on MDP derivatives and their immunological activities is extensive.

It is known that the anti-infective activity of muramyldipeptide derivatives may be enhanced by encapsulating the MDP derivative in liposomes. Liposomes are microscopic vesicles, generally spherically shaped, formed from one or several concentric bilayers (lamellae) of lipid mmolecules having a lipophilic and hydrophilic moiety. Most frequently, liposomes are water insoluble phospholipids which form bilayer structures spontaneously in aqueous suspension. Regardless of the overall shape, the bilayers are organized as closed concentric lamellae, with an aqueous layer separating each lamella from its neighbor. The lamellae of water-soluble liposomes comprise at least one lipid bilayer, the molecules of this layer being oriented so that the hydrophilic functions are in contact with the aqueous phase. Since the liposome layers are separated from each other by an aqueous film, they have a wall-like structure which can be schematically represented, in sections, by molecular composite XY-YX, X representing the hydrophilic portion of the molecule and Y the lipophilic portion. Liposome vesicle size is highly variable and dependent on the composition and method of manufacture, but generally ranges from 25 to 30,000 nm in diameter with a film thickness in the bilayer of 3 to 10 nm.

In recent years, liposomes have attracted widespread interest. Researchers have examined aspects ranging from theoretical physical chemistry to projected applications, particularly in medicine.

The physical chemistry studies have focused on such properties as fluidity, permeability, and molecular organization. These studies are generally motivated by the importance of the lipid bilayer as a structural analog of natural membranes. Liposomes may be used to alter membrane phospholipid and cholesterol content and transfer water-soluble, normally impermeant molecules into cells.

In clinical pharmaceutical research, liposomes have been viewed as a capsule for the possible selective delivery of therapeutic agents such as insulin, enzymes, and anti-tumor drugs.

Liposome-encapsulated muramyldipeptide derivatives have been used in studies wherein noncytotoxic macrophages have been rendered tumoricidal by the interaction of macrophage-activating factor and a free or encapsulated MDP derivative in studies reported by S. Sone and I. J. Fidler, *The Journal of Immunology*, 125 (6), 2454–2460 (1980). See also Sone and Fidler, *Cellular Immunology*, 57, 42–50 (1981); and I. J. Fidler, et al., *Proc. Natl. Acad. Sci. USA*, 78, 1680–1684 (1981). The in vivo studies of Fidler, et al., reported in *Proc. Natl. Acad. Sci. USA* teach that empty multilamellar vesicles with free MDP derivatives do not activate tumoricidal activity in murine alveolar macrophages when the free MDP derivative was administered at the same level as that adequate to cause activation by liposome-encapsulated MDP derivatives. These investigators found that a dose of free MDP derivative 80 times greater than the liposome-encapsulated MDP derivative dose did not activate the tumoricidal activity of murine alveolar macrophages.

It has been shown that the dose of an MDP derivative required for efficacy in protecting mice from bacterial or yeast infections can be reduced significantly by encapsulating the derivative in liposomes. For example, to achieve protection against *Candida albicans* yeast infection in mice, the MDP derivative dose was reduced by approximately 15-fold by encapsulating the MDP derivative in multilamellar liposome vesicles. Efficacy is also related to the liposome composition. This increased efficacy was only achieved when the liposome-encapsulated MDP derivative was given by intravenous injection, which allows the liposomes to be targeted to the phagocytic cells of the reticuloendothelial system. (See E. B. Fraser-Smith, et al., ASM meeting, March 1982.)

It has now been determined that this same increased efficacy can be achieved without actually encapsulating the derivative in liposomes, and without other physical association of the derivative with liposomes (such as association with the lipid bilayers) but by simply co-administering the MDP derivative with liposomes. The derivative can either be mixed with the preformed liposomes prior to injection, or the derivative injection may be preceded or followed by injection of the liposomes. Such co-administration of liposomes and free MDP derivatives provides essentially the same anti-infective activity as that obtained with the same dose of liposome-encapsulated MDP derivative, whereas administration of MDP derivative alone is ineffective at a similar concentration and does not impart anti-infective activity on an equivalent basis until the dose is increased by at least an order of magnitude.

Thus, one advantage of the invention is that one may obtain an enhanced anti-infective activity without introducing the desired MDP derivative during the liposome preparation, as is required by methods in the art.

SUMMARY OF THE INVENTION

One aspect of this invention is a method for enhancing the anti-infective activity of a muramyldipeptide derivative, which method comprises co-administration of an unencapsulated muramyldipeptide (MDP) derivative with liposomes to a bird or mammal. This method has utility for any water-soluble muramyldipeptide derivative and can be carried out in combination with any liposomes prepared from pharmaceutically acceptable material regardless of physical type or size.

Another aspect of the invention is the method of producing or increasing resistance to infection by administering to a bird or mammal a composition comprising an effective amount of an MDP derivative and a sufficient amount of liposomes, with the proviso that the MDP derivative is not encapsulated in or physically attached to the liposomes.

DEFINITIONS

The term "enhancing" or "enhancement" as used herein means that for a given anti-infective response in a subject, a smaller amount of MDP derivative will be needed to effectuate that response than if the MDP derivative was administered without liposomes. The amount of MDP derivative necessary to achieve enhancement will vary with factors including the MDP derivative efficacy, the physical form and chemical composition of the liposome used, and the liposome concentration.

The term "co-administration" refers to the administration of liposomes and an MDP derivative as a mixture to a bird or mammal, where the MDP derivative is not encapsulated in or physically attached to the liposomes.

The term "bird or mammal" includes humans, domestic birds such as chickens, turkeys, and the like, domestic mammals such as cattle, horses, swine, dogs, cats, and the like, as well as wild birds and mammals.

An "effective amount" of an MDP derivative is that amount of MDP derivative which, when administered with a sufficient amount of liposomes, increases the subject's ability to withstand or fend off an infection by bacteria, yeast, fungi, protozoa, molds, actinomycetes, and the like. The effectiveness of this method in increasing the subject's ability to withstand or fend off infection (i.e., enhancing the anti-infective activity of MDP derivatives) is shown by treating test animals such as mice with liposomes and an MDP derivative, waiting for an appropriate time to allow a cellular response to be effected, and then challenging the subjects with an intravenous injection of a usually lethal dose of bacteria, yeast, or the like. Survival time is then used as a measure of efficacy.

A "sufficient amount" of liposomes is that amount which enhances the anti-infective activity of an MDP derivative. It has been found that the effective amount of MDP derivative when co-administered with liposomes is approximately equal to that amount of liposome-encapsulated MDP derivative necessary to elicit a similar anti-infective response. Thus, as a first approximation, a "sufficient amount" of liposomes is that amount which would be necessary to encapsulate the MDP derivative to be administered. However, it should be understood that greater or lesser amounts of liposomes may be required, depending on the liposomes and MDP derivatives employed.

This method has utility for the full spectrum of situations and circumstances where muramyldipeptide derivatives have anti-infective utility. As used herein, "anti-infective" activity refers to the ability of the subject to withstand and combat invasion and multiplication of microorganisms in body tissues. Such infections often result in local cellular injury due to competitive metabolism, toxins, intracellular replication, or antigen-antibody response. The immunological response may be transient or prolonged, and consists of a cellular response (delayed hypersensitivity) and/or the production of specific (immunoglobulin) antibodies to the components of the infecting organism or its toxins.

For the purpose of this invention, the phrase "MDP derivative" refers to all peptidoglycans capable of enhancing the cellular antigenicity response in mammals are includes the muramyldipeptide N-acetylmuramyl-L-alanyl-D-isoglutamine, and analogs and derivatives thereof as set out above.

The term "mixed" refers to the case wherein substituted carboxyl groups are substituted differently, e.g., where one carboxyl is in the form of the amide and the other in the form of an ester.

The term "alkyl" means a saturated branched or unbranched hydrocarbon chain containing 1–22 carbon atoms.

"Lower alkyl" means a branched or unbranched saturated hydrocarbon chain containing 1–4 carbon atoms.

"Acyl" means RC(O)— where "R" is alkyl as defined above.

"Aryl" means phenyl or phenyl lower alkyl, (e.g., benzyl) containing a total of 6 to 15 carbon atoms.

"Substituted" means the that the alkyl, acyl, or aryl radical is substituted with one or more of the following: —OH, —OR$_6$, —OC(O)R$_6$, —C(O)R$_6$, —NH$_2$, —NHR$_6$, or —N(R$_6$)$_2$, where "R$_6$" is lower alkyl as defined above.

"Aminoacyl" refers to an α-amino acid containing less than 12 carbon atoms.

The term "PBS" refers to phosphate-buffered saline lacking divalent cations (e.g., Ca$^{++}$).

The wavy lines in chemical formulae represent the alpha or beta configuration or mixtures thereof. Where one wavy line is alpha the other is beta.

DETAILED DESCRIPTION AND PREFERRED EMBODIMENTS

The broadest aspect of the present invention is a method for enhancing the anti-infective activity of a muramyldipeptide derivative by co-administering said derivative with liposomes.

A preferred embodiment of the invention is the method wherein the MDP derivative is a compound of formula I or a pharmaceutically acceptable salt thereof:

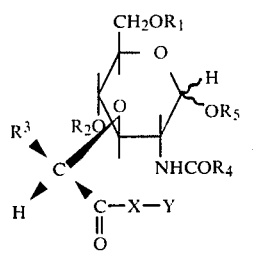

wherein
$R_1$ is hydrogen or acyl;
$R_2$ is hydrogen or acyl;
$R_3$ is hydrogen or lower alkyl;
$R_4$ is alkyl, substituted alkyl, aryl, or substituted aryl;
$R_5$ is hydrogen, alkyl, substituted alkyl, aryl, or substituted aryl;
X is an aminoacyl moiety selected from the group consisting of

| | |
|---|---|
| L-alanyl, | L-tryptophanyl, |
| L-valyl, | L-lysyl, |
| L-leucyl, | L-ornithyl, |
| L-isoleucyl, | L-arginyl, |
| L-α-aminobutyryl, | L-histidyl, |
| L-seryl, | L-glutamyl, |
| L-threonyl, | L-glutaminyl, |
| L-methionyl, | L-aspartyl, |
| L-cysteinyl, | L-asparaginyl, |
| L-phenylalanyl, | L-prolyl, |
| L-tyrosyl, | L-hydroxyprolyl; and |

Y is D-glutamic or D-aspartic acid, or a mono-, di-, or mixed alkyl ester, amide, or lower alkyl amide thereof.

More preferred is the method wherein $R_1$, $R_2$, and $R_5$ are hydrogen, and $R_4$ is methyl. Still more preferred is the method wherein X is L-valyl, L-alanyl, L-threonyl, L-seryl, or L-α-aminobutyryl and Y is D-isoglutamine.

Most preferred are the species wherein $R_3$ is methyl, especially the derivatives:
N-acetylmuramyl-L-alanyl-D-isoglutamine;
N-acetylmuramyl-L-α-aminobutyryl-D-isoglutamine;
N-acetylmuramyl-L-valyl-D-isoglutamine; and
N-acetylmuramyl-L-seryl-D-isoglutamine.

Also preferred are the species wherein $R_3$ is hydrogen, especially the derivatives:
N-acetyldesmethylmuramyl-L-alanyl-D-isoglutamine; and
N-acetyldesmethylmuramyl-L-α-aminobutyryl-D-isoglutamine.

Another aspect of the invention is the method of enhancing anti-infective activity (producing or increasing resistance to infection) by administering to a bird or mammal a composition comprising an effective amount of an MDP derivative and a sufficient amount of liposomes.

A preferred embodiment of the invention is the method of enhancing anti-infective activity wherein the MDP derivative is a compound of formula I.

More preferred is the method wherein $R_1$, $R_2$, and $R_5$ are hydrogen, and $R_4$ is methyl. Still more preferred is the method wherein X is L-valyl, L-alanyl, L-threonyl, L-seryl, or L-α-aminobutyryl and Y is D-isoglutamine.

Most preferred are the species wherein $R_3$ is methyl, where the MDP derivatives are:
N-acetylmuramyl-L-alanyl-D-isoglutamine;
N-acetylmuramyl-L-α-aminobutyryl-D-isoglutamine;
N-acetylmuramyl-L-valyl-D-isoglutamine; and
N-acetylmuramyl-L-seryl-D-isoglutamine.

Also preferred are the species wherein $R_3$ is hydrogen, where the MDP derivatives are:
N-acetyldesmethylmuramyl-L-alanyl-D-isoglutamine; and
N-acetyldesmethylmuramyl-L-α-aminobutyryl-D-isoglutamine.

MDP derivatives are known and described in the periodical and patent literature. See, for example, Belgian Pat. Nos. 834,753, 834,754, 847,103, 849,214; German Pat. Nos. 2,710,455, 2,922,533, 2,747,379, 2,912,865; French Pat. Nos. 2,355,505, 2,358,159 and 2,375,249; European Patent Office Pat. Nos. 4,512 and 2,677; Japanese Pat. Nos. 54/063016, 54/073729 and 55/019236. See also U.S. Pat. Nos. 4,082,735 and 4,082,736, incorporated herein by reference and made a part hereof. The synthesis of N-acetylmuramyl-L-alanyl-D-isoglutamine and derivatives thereof can be found in *Biochem. Biophys. Res. Comm.*, 66, 1316 (1975) by C. P. Messer and P. Sinay and in the cited patents.

Liposomes are most frequently prepared from phospholipids, many of which form lipid bilayer structures spontaneously in aqueous solution, but any molecule having a lipophilic moiety and a hydrophilic moiety, commonly known as a surfactant, can be used to prepare liposomes. For the purposes of this invention the term "liposome" is intended to cover any concentric lipid bilayer structure consisting of closed concentric lamellae enclosing one or more aqueous-containing compartments and prepared from pharmaceutically acceptable compounds having surfactant properties.

Liposomes can be divided into three categories based on their overall size and the nature of the lamellar structure. To describe these physical classifications, the nomenclature developed at the New York Academy of Sciences meeting on "Liposomes and Their Use in Biology and Medicine," of September 1977 will be used. The three classes are multilamellar vesicles (MLV), small unilamellar vesicles (SUV) and large unilamellar vesicles (LUV). Small unilamellar vesicles range in diameter from approximately 20 to 50 nm and consist of a single lipid bilayer surrounding an aqueous compartment. It is characteristic of SUVs that a large amount (about 70%) of the total lipid is located in the outer layer of the vesicle. A disadvantage of SUVs is that the small radius of curvature imposes strain in the lipid molecule packing, resulting in metastable SUVs in some circumstances.

Several methods are available for preparing SUVs, but the most widely used is ultrasonic dispersion (sonication) either by the immersion of a vibrating metal probe directly into a suspension of multilamellar vesicles or the suspension of sealed vials containing MLVs in an ultrasonic cleaning bath. Sonication is usually carried out at a controlled temperature in an inert atmosphere such as nitrogen or argon to prevent oxidative degradation and hydrolysis of the lipid materials.

The most frequently encountered and easily prepared liposomes are multilamellar vesicles (MLVs). Where SUVs are single compartmental vesicles of fairly uniform size, MLVs vary greatly in size up to about 10,000 nm and are multicompartmental in their structure. Preparation is fairly simple and straightforward, and involves dissolving the appropriate lipids in an organic solvent which is then evaporated, leaving behind a thin film of dried lipid on the surface of the container. An aqueous solution is then introduced into the container which is agitated to free lipid material from the sides of the container and to disperse lipid aggregates.

Large unilamellar vesicles (LUV) are so named because of their large diameter which ranges from about 600 nm to upwards of 30 microns. Such vesicles may contain one or more bilayers. Several methods are available for preparing LUVs. For example, slow hydration of a thin layer of lipid with distilled water or an aqueous solution of non-electrolyte will result in the formation of LUVs.

A variety of methods for preparing various liposome forms have been described in the periodical literature. A number of patented procedures exist for the preparation of liposomes, any of which may be used in the practice of this invention. It should be noted that because active compounds are not encapsulated in the practice of the invention, the simplest methods of liposome preparation may be employed. Only in those instances where it is desired to precisely control the type and size of liposome will it be necessary to resort to preparative methods which are more complicated than simply dissolving lipids in an organic solvent, removing the solvent completely and hydrating the lipids with an appropriate MDP derivative-free solvent.

The practitioner of this invention who may wish to precisely control the number of layers and vesicle size of the liposomes employed is referred to reviews by Pagano and Weinstein, *Ann. Rev. Biophysic. Bioeng.*, 7, pp. 435–68 (1978), and Szoka and Papahadjopoulos, *Ann. Rev. Biophysic. Bioeng.*, 9, 467–508 (1980), and to a number of patents for preparing liposomes, for example, U.S. Pat. Nos. 4,229,360, 4,224,179, 4,127,344, 4,193,893, 4,217,344, 4,241,046, 4,078,052 and 4,235,871, all of which are hereby incorporated by reference. Any or all of the liposome-forming procedures described in these patents may be used in preparing liposomes for the practice of this invention. However, it should be understood that preparative methodology in no way limits the scope of this invention as it is the liposome itself which is of importance to this invention, and not how the liposome was realized or prepared.

Furthermore, liposomes prepared with a recognition macromolecule to bind liposomes selectively to a particular cell fall within the scope of this invention. A number of such recognition macromolecules, for example, antibodies, plant lectins, desialylated glycoproteins and the like have been attached to liposomes by non-specific forces or by covalent linkage sites. A review of some of the work in this area can be found in the Pagano and Weinstein reference recited above, and in U.S. Pat. No. 4,310,505, incorporated herein by reference.

Liposomes may also be prepared from any surfactant or combinations of surfactants. However, for the practice of this invention, only those surfactants which are pharmaceutically acceptable may be used. That is, useful surfactants should not have or exhibit a deleterious or untoward effect on the host to which they were administered either systemically or at the site of administration.

To form the lamellar phase, a single surfactant material or mixtures can be employed. Suitable surfactants are, e.g., ternary or complex lipids, glycerides, cerides, etholides and steroids, namely one of several compounds wherein the hydrophilic group is a phosphate, carboxylate, sulfate, amino, hydroxyl or choline group, and the lipophilic group is alkyl or alkylenyl, polyoxyalkylene or an alkyl group substituted with at least one aromatic or cycloalkyl group.

The liposomes may be anionic, basic or neutral depending upon the choice of hydrophilic group. For instance, when a phosphate or a sulfate group is used the resulting liposome will be anionic. When amino-containing surfactants are used, the liposomes will have a positive charge, or be cationic liposomes, and when polyethyleneoxy or glycol groups are present in the surfactant, neutral liposomes will be obtained. Compounds suitable for forming liposomes may be found in references including *McCutcheon's Detergents and Emulsifiers* and *McCutcheon's Functional Materials*, Allured Pub. Company, Ridgewood, N.J., U.S.A.

Preferred surfactants are phospholipid-related materials including lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, phosphatidylcholine and dipalmitoylphosphatidylcholine. Additional non-phosphorous-containing lipids are for instance stearylamine, dodecylamine, hexadecylamine, cetyl palmitate, glyceryl ricinoleate, hexadecyl stearate, isopropyl myristate, amphoteric acrylic polymers, triethanolamine-lauryl sulphate, alkyl-aryl sulfonates, polyethoxylated fatty acid amides and the like.

Various additives can be combined with the surfactant so as to modify its permeability characteristics or the superficial charge of the resulting liposomes. Representative additives include long chain alcohols and diols, sterols, (e.g., cholesterol), long chain amines and their quaternary ammonium derivatives, dihydroxyalkylamines, polyoxyethylenated fatty amines, esters of long chain amino alcohols, their salts and quaternary ammonium derivatives, phosphoric esters of fatty alcohols, (e.g., sodium dicetyl phosphate), alkylsulfates, (e.g., sodium cetyl sulfate), and certain polymers such as polypeptides and proteins.

It should be understood that the surfactant compositions, with or without additives, used to prepare liposomes may be a combination of surfactants, and may be derived from any natural or synthetic source, so long as the resulting liposomes are non-toxic and pharmaceutically acceptable.

ADMINISTRATION AND FORMULATION

The method of the invention involves the co-administration of liposomes and free MDP derivatives. Parenteral administration is usually either subcutaneous, intramuscular or intravenous injection. It is preferred to practice the invention using parenteral administration, particularly by injection, especially by intravenous injection. Injectable formulations may be prepared in conventional forms, as liquid solutions or suspensions, solid forms suitable for solution or suspension in liquid prior to injection, and as emulsions. Suitable excipients are, for example, water, saline, dextrose, glycerol, ethanol and the like. In addition, if desired, the pharmaceutical compositions to be administered may also contain non-toxic auxiliary substances such as pH buffering agents and the like, such as for example, sodium acetate.

The effective dose of MDP derivative will vary depending upon the activity of the particular compound employed. Precise figures for each and every MDP derivative are not presently known. However, the effective dosage generally will fall in the range of 0.0001 mg/kg/dose to 30 mg/kg/dose, preferably between 0.1 and 5 mg/kg/dose. In general, the amount of liposome material needed to effectively enhance the anti-infective activity of an effective amount of free (unencapsulated) MDP derivative will be similar to the amount necessary to encapsule an effective MDP derivative dose. This amount will usually be between about 0.1 and 1,000 micromoles of surfactant per kg body weight per dose, through it should be understood that there may be instances where more or less liposome-forming material can be used and still realize the enhanced anti-infective response of this invention.

The dosage regime may consist of one or more doses per day, but it is preferred to minimize the number of injections, hence a single dose is most preferred.

It is most preferable to prepare the liposomes, mix in the MDP derivative and administer the mixture in a single injection..

EXAMPLE 1

Multilamellar vesicles (MLVs) were formed by drying down egg phosphatidylcholine and brain phosphatidylserine (7:3 molar ratio) on the inside of a flask. Phosphate-buffered saline lacking divalent cations (PBS) was added (1 ml per 20 micromoles phospholipid), and the flask shaken, either by hand or with a mechanical shaker, until the lipid film was dispersed. When N-acetylmuramyl-L-$\alpha$-aminobutyryl-D-isoglutamine (abu-MDP) was to be encapsulated, it was included in the aqueous solution before addition to the lipid film. The vesicles formed as the result of shaking the aqueous solution which contained MDP derivative were washed to remove unencapsulated MDP derivative, pelleted by centrifugation at 30,000$\times$g for 20–30 min, and then resuspended in PBS. MLV preparations made without MDP derivative were either pelleted and resuspended as described, or were used without further treatment.

Mice were injected intravenously with liposomes (4 micromoles phospholipid) and also with free abu-MDP (2–4 mg/kg). The abu-MDP was injected at the same time as the liposome injection. Injections were made at 96 and 48 hr prior to challenge with *Candida albicans* (5$\times$10[6] cells injected intravenously). Control mice were treated with either liposomes only, or abu-MDP only (4 or 60 mg/kg), or abu-MDP (2–4 mg/kg) encapsulated in liposomes, and similarly challenged with *Candida albicans*. Each treatment group contained 20 mice. All mice were monitored daily for number of survivors. Statistical analysis of survival time was computed using Mann Whitney U probability analysis, and the numbers of survivors were statistically compared using Fisher Exact probability analysis.

Study results are presented in Table I below. The same protective activity against *Candida albicans* was obtained whether abu-MDP was encapsulated in MLV or mixed with MLV just prior to treatment. P values, calculated for survival time and number of survivors at the time when controls (treated only with MLV or with saline) first reached 100% dead, were all less than 0.03. By comparison, the treatments with the same concentration of abu-MDP alone were ineffective (P$\geq$0.05). Only when the concentration of free abu-MDP alone was raised to 60 mg/kg was protective activity obtained equivalent to that seen using the lower dose of abu-MDP (2–4 mg/kg) plus MLV.

TABLE I

Survival of mice treated[a] with abu-MDP prior to challenge with *Candida albicans*.

| Compound | abu-MDP dose (mg/kg) | Survival Time (Days) | No. (%) | P values[b] Time | No. | P values[c] Time | No. |
|---|---|---|---|---|---|---|---|
| abu-MDP with MLV | 2 | 5.1 | 32 | <0.002 | 0.007 | >0.1 | 1.0 |
| | 4 | 5.6 | 50 | <0.002 | 0.002 | >0.1 | 0.6 |
| abu-MDP in MLV | 2 | 5.1 | 36 | <0.002 | 0.002 | — | — |
| | 4 | 6.1 | 62 | <0.002 | 0.002 | — | — |
| Saline in MLV | 0 | 3.0 | 0 | —d | — | — | — |
| abu-MDP with MLV | 4 | 7.2 | 65 | <0.002 | 0.005 | >0.1 | 0.9 |
| abu-MDP in MLV | 4 | 7.2 | 68 | <0.002 | 0.002 | — | — |
| Saline in MLV | 0 | 5.3 | 18 | — | — | — | — |
| abu-MDP | 4 | 4.4 | 0 | NS | NS | — | — |
| abu-MDP | 60 | 6.9 | 45 | 0.01 | 0.05 | — | — |
| Saline | 0 | 3.6 | 0 | — | — | — | — |

[a]Mice received two treatments, at days 4 and 2 before infection. "With" = abu-MDP co-administered with but not encapsulated in MLV; "in" = encapsulated in MLV.
[b]Comparison was to saline in MLV control, or saline control for groups which did not receive MLV. NS indicates P>0.05 which was considered not significant.
[c]Comparison was to abu-MDP encapsulated in MLV at same dose level.
[d]Not applicable

EXAMPLE 2

A second experiment was performed by the method described in Example 1, except that the mice were given a single pre-infection treatment at 72 hr prior to challenge, instead of treatments at 96 and 48 hr prior to challenge as in Example 1. Results are presented in Table II, below. Although the overall protective activity was not as pronounced with one pre-infection treatment, the same conclusion was reached: treating with abu-MDP mixed with MLV (but not encapsulated in MLV) resulted in the same anti-infective activity as when the drug was encapsulated in the MLV (P$\leq$0.05).

TABLE II

Survival of mice treated[a] with abu-MDP prior to challenge with *Candida albicans*.

| Compound | abu-MDP dose (mg/kg) | Survival Time (Days) | No. (%) | P values[b] Time | No. | P values[c] Time | No. |
|---|---|---|---|---|---|---|---|
| abu-MDP with MLV | 4 | 6.4 | 30 | 0.01 | NS | >0.1 | 1.0 |
| abu-MDP in MLV | 4 | 6.7 | 35 | 0.002 | 0.02 | — | — |
| Saline in MLV | 0 | 4.4 | 5 | d | — | — | — |
| abu-MDP | 4 | 5.2 | 0 | NS | NS | — | — |
| abu-MDP | 60 | 6.4 | 32 | 0.01 | NS | — | — |
| Saline | 0 | 4.9 | 0 | — | — | — | — |

[a]Mice received one treatment, at day 3 before infection. "With" = abu-MDP co-administered with but not encapsulated in MLV; "in" = encapsulated in MLV.
[b]Comparison was to saline in MLV control, or saline control for groups which did not receive MLV. NS indicates P>0.05, which was considered not significant.
[c]Comparison was to abu-MDP encapsulated in MLV.
[d]Not applicable

EXAMPLE 3

MLVs were prepared as described above, hydrating the dried lipid film with PBS. These pre-formed liposomes were then mixed with unencapsulated MDP compound spiked with tritiated N-acetyldesmethylmuramyl-L-alanyl-D-isoglutamine ($^3$H-desMDP). The liposome/MDP derivative mixture was washed and pelleted, and the final liposome pellet resuspended in PBS. The radioactivity in the liposome fraction was determined, as well as the radioactivity in the aqueous supernatant from the washing and pelleting steps. The results are presented in Table III. These results show that essentially 100% of the $^3$H label remained in the supernatant and was not incorporated into the liposomes. Thus, MDP compounds are not incorporated into or attached to liposomes in the practice of the invention.

TABLE III

| Sample | cpm/0.1 ml | % of Total |
| --- | --- | --- |
| aqueous fraction | 557,610 | 100 |
|  | 562,800 |  |
| liposome fraction | 1,462 | 0.2 |
|  | 1,304 |  |

EXAMPLE 4

The following is a representative formulation of a composition for use in the practice of the invention, suitable for intravenous injection.

| | |
| --- | --- |
| dioleoyl phosphatidylcholine | 14.0 μmoles |
| dioleoyl phosphatidylglycerol | 6.0 μmoles |
| PBS | 1.0 ml |
| abu-MDP | 0.2 mg |

The dioleoyl phosphatidylcholine and dioleoyl phosphatidylglycerol are dried down on the inside of a flask. Then, 0.5 ml phosphate-buffered saline lacking divalent cations (PBS) is added, and the flask shaken by hand until the lipid film is dispersed. N-acetylmuramyl-L-α-aminobutyryl-D-isoglutamine (abu-MDP), dissolved in 0.5 ml PBS is then added to the liposome suspension, affording an injectable formulation of the invention.

Another formulation is prepared as follows:

| | |
| --- | --- |
| egg phosphatidylcholine | 14.0 μmoles |
| brain phosphatidylserine | 6.0 μmoles |
| PBS | 1.0 ml |
| abu-MDP | 0.2 mg |

The egg phosphatidylcholine and brain phosphatidylserine are dried down on the inside of a flask. Then, 0.5 ml phosphate-buffered saline lacking divalent cations (PBS) is added, and the flask shaken by hand until the lipid film is dispersed. N-acetylmuramyl-L-α-aminobutyryl-D-isoglutamine (abu-MDP), dissolved in 0.5 ml PBS is then added to the liposome suspension, affording an injectable formulation of the invention.

What is claimed is:

1. A method for enhancing the anti-infective activity of a muramyldipeptide derivative, which method comprises parenterally co-administering an effective amount of a muramyldipeptide derivative ("MDP derivative") and an anti-infective activity enhancing amount of liposomes to a bird or mammal wherein said MDP derivative is a compound of formula I or a pharmaceutically acceptable salt thereof:

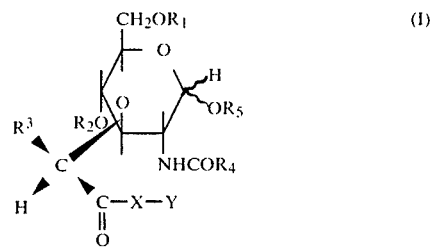

wherein
$R_1$ is hydrogen or acyl of 1–22 carbon atoms;
$R_2$ is hydrogen or acyl of 1–22 carbon atoms;
$R_3$ is hydrogen or lower alkyl of 1–4 carbon atoms;
$R_4$ is alkyl of 1–22 carbon atoms, phenyl, phenyl-lower alkyl containing a total of 6–15 carbon atoms, where alkyl, phenyl, and phenyl-lower alkyl may be substituted with one or more of the following: —OH, —OR$_6$, —OC(O)R$_6$, —C(O)R$_6$, —NH$_2$, —NHR$_6$, or —N(R$_6$)$_2$, where R$_6$ is alkyl of 1–4 carbon atoms; p1 $R_5$ is hydrogen, alkyl of 1–22 carbon atoms, phenyl, phenyl-lower alkyl containing a total of 6–15 carbon atoms, where alkyl, phenyl, and phenyl-lower alkyl may be substituted with one or more of the following: —OH, —OR$_6$, —OC(O)R$_6$, —C(O)R$_6$, —NH$_2$, —NHR$_6$, or —N(R$_6$)$_2$, where R$_6$ is alkyl of 1–4 carbon atoms;
X is an aminoacyl moiety selected from the group consisting of

| | |
| --- | --- |
| L-alanyl, | L-tryptophanyl, |
| L-valyl, | L-lysyl, |
| L-leucyl, | L-ornithyl, |
| L-isoleucyl, | L-arginyl, |
| L-α-aminobutyryl, | L-histidyl, |
| L-seryl, | L-glutamyl, |
| L-threonyl, | L-glutaminyl, |
| L-methionyl, | L-aspartyl, |
| L-cysteinyl, | L-asparaginyl, |
| L-phenylalanyl, | L-prolyl, |
| L-tyrosyl, | L-hydroxyprolyl; and |

Y is D-glutamic or D-aspartic acid, or an (alkyl of 1–22 carbon atoms)ester thereof, a di(alkyl of 1–22 carbon atoms)ester thereof, an amide thereof, an (alkyl of 1–4 carbon atoms)amide thereof, a di(alkyl of 1–4 carbon atoms)amide thereof, or an (alkyl of 1–22 carbon atoms)ester-(alkyl of 1–4 carbon atoms)amide thereof;
with the proviso that the MDP derivative is not encapsulated in or physically attached to the liposomes.

2. The method of claim 1 wherein R$_1$ and R$_2$ are hydrogen.

3. The method of claim 2 wherein R$_5$ is hydrogen.

4. The method of claim 3 wherein R$_4$ is methyl.

5. The method of claim 4 wherein Y is D-isoglutamine or D-aspartamine.

6. The method of claim 5 wherein X is L-valyl, L-alanyl, L-threonyl, L-seryl, or L-α-aminobutyryl and Y is D-isoglutamine.

7. The method of claim 6 wherein the MDP derivative is
N-acetylmuramyl-L-alanyl-D-isoglutamine;

N-acetyldesmethylmuramyl-L-alanyl-D-isoglutamine;

N-acetylmuramyl-L-α-aminobutyryl-D-isoglutamine;

N-acetyldesmethylmuramyl-L-α-aminobutyryl-D-isoglutamine;

N-acetylmuramyl-L-valyl-D-isoglutamine; or

N-acetylmuramyl-L-seryl-D-isoglutamine.

8. The method of claim 7 wherein the MDP derivative is N-acetylmuramyl-L-alanyl-D-isoglutamine.

9. The method of claim 7 wherein the MDP derivative is N-acetyldesmethylmuramyl-L-alanyl-D-isoglutamine.

10. The method of claim 7 wherein the MDP derivative is N-acetylmuramyl-L-α-aminobutyryl-D-isoglutamine.

11. The method of claim 7 wherein the MDP derivative is N-acetyldesmethylmuramyl-L-α-aminobutyryl-D-isoglutamine.

12. The method of claim 7 wherein the MDP derivative is N-acetylmuramyl-L-valyl-D-isoglutamine.

13. The method of claim 7 wherein the MDP derivative is N-acetylmuramyl-L-seryl-D-isoglutamine.

14. A method of producing or increasing resistance to infection by parenterally administering to a bird or mammal a composition comprising an effective amount of a muramyldipeptide derivative ("MDP derivative") and an anti-infective activity enhancing amount of liposomes, with the proviso that the MDP derivative is not encapsulated in or physically attached to the liposomes, wherein said MDP derivative is a compound of formula I or a pharmaceutically acceptable salt thereof:

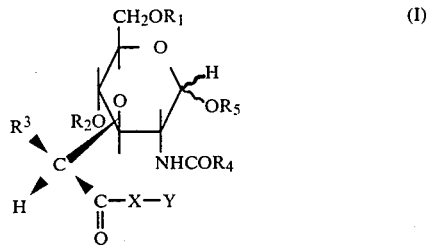

wherein $R_1$ is hydrogen or acyl of 1–22 carbon atoms;

$R_2$ is hydrogen or acyl of 1–22 carbon atoms;

$R_3$ is hydrogen or lower alkyl of 1–4 carbon atoms;

$R_4$ is alkyl of 1–22 carbon atoms, phenyl, phenyl-lower alkyl containing a total of 6–15 carbon atoms, where alkyl, phenyl, and phenyl-lower alkyl may be substituted with one or more of the following: —OH, —OR$_6$, —OC(O)R$_6$, —C(O)R$_6$, —NH$_2$, —NHR$_6$, or —N(R$_6$)$_2$, where R$_6$ is alkyl of 1–4 carbon atoms;

$R_5$ is hydrogen, alkyl of 1–22 carbon atoms, phenyl, phenyl-lower alkyl containing a total of 6–15 carbon atoms, where alkyl, phenyl, and phenyl-lower alkyl may be substituted with one or more of the following: —OH, —OR$_6$, —OC(O)R$_6$, —C(O)R$_6$, —NH$_2$, —NHR$_6$, or —N(R$_6$)$_2$, where R$_6$ is alkyl of 1–4 carbon atoms;

X is an aminoacyl moiety selected from the group consisting of

| | |
|---|---|
| L-alanyl, | L-tryptophanyl, |
| L-valyl, | L-lysyl, |
| L-leucyl, | L-ornithyl, |
| L-isoleucyl, | L-arginyl, |
| L-α-aminobutyryl, | L-histidyl, |
| L-seryl, | L-glutamyl, |
| L-threonyl, | L-glutaminyl, |
| L-methionyl, | L-aspartyl, |
| L-cysteinyl, | L-asparaginyl, |
| L-phenylalanyl, | L-prolyl, |
| L-tyrosyl, | L-hydroxyprolyl; and |

Y is D-glutamic or D-aspartic acid, or an (alkyl of 1–22 carbon atoms)ester thereof, a di(alkyl of 1–22 carbon atoms)ester thereof, an amide thereof, an (alkyl of 1–4 carbon atoms)amide thereof, a di(alkyl of 1–4 carbon atoms)amide thereof, or an (alkyl of 1–22 carbon atoms)ester-(alkyl of 1–4 carbon atoms)amide thereof;

with the proviso that the MDP derivative is not encapsulated in or physically attached to the liposomes.

15. The method of claim 14 wherein $R_1$ and $R_2$ are hydrogen.

16. The method of claim 15 wherein $R_5$ is hydrogen.

17. The method of claim 16 wherein $R_4$ is methyl.

18. The method of claim 17 wherein Y is D-isoglutamine or D-aspartamine.

19. The method of claim 18 wherein X is L-valyl, L-alanyl, L-threonyl, L-seryl, or L-α-aminobutyryl and Y is D-isoglutamine.

20. The method of claim 19 wherein the MDP derivative is

N-acetylmuramyl-L-alanyl-D-isoglutamine;

N-acetyldesmethylmuramyl-L-alanyl-D-isoglutamine;

N-acetylmuramyl-L-α-aminobutyryl-D-isoglutamine;

N-acetyldesmethylmuramyl-L-α-aminobutyryl-D-isoglutamine;

N-acetylmuramyl-L-valyl-D-isoglutamine; or

N-acetylmuramyl-L-seryl-D-isoglutamine.

21. The method of claim 20 wherein the MDP derivative is N-acetylmuramyl-L-alanyl-D-isoglutamine.

22. The method of claim 20 wherein the MDP derivative is N-acetyldesmethylmuramyl-L-alanyl-D-isoglutamine.

23. The method of claim 20 wherein the MDP derivative is N-acetylmuramyl-L-α-aminobutyryl-D-isoglutamine.

24. The method of claim 20 wherein the MDP derivative is N-acetyldesmethylmuramyl-L-α-aminobutyryl-D-isoglutamine.

25. The method of claim 20 wherein the MDP derivative is N-acetylmuramyl-L-valyl-D-isoglutamine.

26. The method of claim 20 wherein the MDP derivative is N-acetylmuramyl-L-seryl-D-isoglutamine.

* * * * *